United States Patent
Andrulis (10) Patent No.: US 9,522,941 B2
(45) Date of Patent: Dec. 20, 2016

(54) METHODS AND COMPOSITIONS RELATED TO CHROMATIN-ASSOCIATED PROTEINS AND OTHER FACTORS

(75) Inventor: Erik D. Andrulis, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1498 days.

(21) Appl. No.: 11/909,677

(22) PCT Filed: Mar. 31, 2006

(86) PCT No.: PCT/US2006/012089
§ 371 (c)(1),
(2), (4) Date: Sep. 25, 2007

(87) PCT Pub. No.: WO2006/107787
PCT Pub. Date: Oct. 12, 2006

(65) Prior Publication Data
US 2010/0184961 A1    Jul. 22, 2010

Related U.S. Application Data (60) Provisional application No. 60/667,754, filed on Apr. 1, 2005.

(51) Int. Cl.
| | |
|---|---|
| C07H 21/04 | (2006.01) |
| G01N 33/48 | (2006.01) |
| G01N 33/483 | (2006.01) |
| C07K 14/435 | (2006.01) |
| D01F 6/74 | (2006.01) |
| G01N 33/68 | (2006.01) |

(52) U.S. Cl.
CPC ........... *C07K 14/43581* (2013.01); *D01F 6/74* (2013.01); *G01N 33/6803* (2013.01); *G01N 33/6875* (2013.01); *Y10T 428/2913* (2015.01)

(58) Field of Classification Search
CPC .. A61K 38/16; C07K 2319/00; G01N 33/6875
USPC ....................................................... 530/358
See application file for complete search history.

(56) References Cited

PUBLICATIONS

Grossman et al. Sucrose gradient centrifugation sedimentation standards: a simplified technique. Clin Chem. Jul. 1980:26(8)1235.*

Washburn et al. Large-scale analysis of the yeast proteome by multidimensional protein identification technology. Nat Biotechnol. Mar. 2001:19(3):242-7.*

Zheng et al. Intra- and inter-nucleosomal protein-DNA interactions of the core histone tail domains in a model system. J Biol Chem. Jun. 27, 2003;278(26):24217-24. Epub Apr. 15, 2003.*

Galande et al. Linking chromatin architecture to cellular phenotype: BUR-binding proteins in cancer. J Cell Biochem Suppl. 2000;Suppl 35:36-45.*

Splinter et al. 3C Technology: Analyzing the Spatial Organization of Genomic Loci In Vivo. Methods in Enzymology, vol. 375, 2003, pp. 493-507.*

Griffith, D. Visualization of prokaryotic DNA in a rgularly condensed chromatin-like fiber. PNAS 73(2): 563-567, 1976.*

Wallberg et al. p300 and PCAF Act Cooperatively to Mediate Transcriptional Activation from Chromtain Templates by Notch Intracellular Domains In Vitro. Mol. and Cell. Biol. Nov. 2002, vol. 22, pp. 7812-7819.

Jackson. Formaldehyde Cross-Linking for Studying Nucleosomal Dynamics. Methods in Enzym. 1999. vol. 17, pp. 125-139, especially abstract, figure 1, pp. 127-128 and p. 138.

Sperling et al. Photchemical cross-linking of histones to DNA in nucleosomes. Nuc. Acid Res. Aug. 1978, vol. 5 No. 8, pp. 2755-2773, especially abstract and materials & methods.

Augenlicht et al. Appearance of Rapidly labeled High Molecular Weight RNA in Nuclear Ribonuleoprotein. J. Biol. Chem. May 1976, vol. 251 No. 9, pp. 2592-2599, especially abstract and materials & methods.

Pray-Grant et al. The Novel SLIK Histone Acetyltransfer Complex Functions in the Yeast Retrograde Response Pathway. Mol. and Cell. Biol. Dec. 2002, vol. 22. No. 24, pp. 8774-8786.

* cited by examiner

*Primary Examiner* — Nancy J Leith
(74) *Attorney, Agent, or Firm* — Tarolli, Sundheim, Covell & Tummino LLP (57) ABSTRACT

Chromatin-associated proteins and other factors and their related methods and compositions are isolated and identified.

8 Claims, 7 Drawing Sheets

METHODS AND COMPOSITIONS RELATED TO CHROMATIN-ASSOCIATED PROTEINS AND OTHER FACTORS

BACKGROUND OF THE INVENTION

DNA in the eukaryotic nucleus is packaged into chromatin. The basic component of chromatin is the nucleosome, comprised of an octamer of the core histones H2A, H2B, H3, and H4 encircled by 146 base pairs of DNA. Nucleosomes, in turn, can be tightly packaged by the linker histone H1, which are then further organized into higher-order structures by additional factors, most of which are not well characterized.

Although the basic building blocks of chromatin are known, the protein factors regulating chromatin structure and function are poorly defined or not yet discovered. Modulation of chromatin structure and composition plays a vital role in a variety of basic cellular processes, such as transcription, DNA repair, replication, and mitosis as well as in large scale events in cells and organisms including, but not limited to development, differentiation, and responses to external stimuli. Defects that disrupt chromatin structure can directly elicit human diseases and cancer. Thus, cataloguing the protein composition of chromatin is desirable in order to facilitate the discovery of novel therapeutic targets to stem the progression of disease states.

Current methods to identify the protein composition, as well as other factors, of chromatin, are inadequate and often inappropriate. For example, genetic analyses in yeast of *Drosophila*, or depletion studies in mammalian cells have identified factors that associate with or regulate chromatin. However, results obtained from these studies are sometimes indirect and oftentimes misleading and thus must be confirmed using additional techniques.

SUMMARY OF THE INVENTION

The present application relates to an isolated chromatome. The isolated chromatome comprises chromatomal proteins and chromatomal factors and less than about 10% non-chromatomal proteins and non-chromatomal factors.

Another aspect of the present application relates to a method for preparing a cross-linked nucleic acid-protein complex. In the method, a cell is contacted with a stabilizer at a concentration and for a period of time effective for stabilizing protein-chromatin complexes. The concentration and the period of time can be selected for specific stabilization of the interactions between chromatin proteins and chromatin. The protein-chromatin complexes are then isolated from the cell. The isolated protein-chromatin complexes form the chromatome.

In an aspect of the invention the stabilizer is a cross-linking agent. The cross-linking agent can comprise formaldehyde, used at a concentration of less than about 1%, and the period of time can be less than about 30 minutes. The protein-chromatin complexes can be isolated by a CsCl gradient.

Another aspect of the present application relates to a method for identifying chromatomal proteins associated with a phenotype of a cell. In the method, a chromatome can be isolated from a cell exhibiting the phenotype. The isolated chromatome can comprise chromatomal proteins and chromatomal factors, and less than about 10% non-chromatomal proteins and non-chromatomal factors. The isolated chromatome can comprise protein-chromatin complexes. The proteins can be isolated from protein-chromatin complexes in the isolated chromatome. The isolated proteins can be identified. The identity of the isolated proteins can be compared with the identity of chromatomal proteins from a cell that does not exhibit the phenotype. The isolated proteins that are different from the identified chromatomal proteins can be associated with the phenotype.

A further aspect of the present application relates to a method for identifying chromatomal proteins and/or chromatomal factors in a cell. In the method, a chromatome is isolated from the cell. The isolated chromatome can comprise chromatomal proteins and chromatomal factors, and less than about 10% non-chromatomal proteins and non-chromatomal factors. The isolated chromatome can comprise protein-chromatin complexes. At least one of proteins from the protein-chromatin complexes and chromatomal factors from the isolated chromatome can be isolated. At least one isolated protein or chromatomal factor can be identified.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 2(A-C) illustrate the purification of chromatin using cesium chloride (CsCl) sedimentation.

DETAILED DESCRIPTION OF THE INVENTION

The present application relates to a method and sophisticated means of analyzing the content of chromatin as well as chromatin proteins and/or factors that may complex with chromatin in a cell.

The present application is based on the technology that optimizes conditions for a protocol known as chromatin immunoprecipitation (ChIP). Basically, CHIP refers to the recovery of formaldehyde cross-linked protein-DNA complexes from cell or nuclear extracts using an antibody towards a protein of interest. The DNA that co-purifies with the protein of interest is then analyzed by PCR.

Formaldehyde cross-linking has been employed successfully by a large number of research groups over the past several. Although cross-linking has been used to examine the specific DNA sequences that co-immunoprecipitate with a given protein (i.e., ChIP), it has not been used to investigate the set of proteins that associate with DNA or chromatin. The high formaldehyde concentrations used in typical ChIP assays create nonspecific protein-protein cross-links and the protein-DNA complexes recovered from a whole cell extract in a typical ChIP assay is very crude.

The present application provides rapid and efficient methods for the isolation and characterization of protein and other factors associated with chromatin in a cell. As used herein in the specification and the claims, the full complement of protein and other factors associated with chromatin in a cell constitutes the "chromatome", and certain methods employed to purify a chromatome are termed "chromatomography". A chromatome of the present application may comprise, in addition to proteins, other factors, for example, DNA, RNA, small molecules, metabolites, which may be termed "chromatomal factor" (e.g., chromatomal protein, chromatome DNA, chromatome RNA, chromatome metabolite, etc.).

Additionally, the present application provides compositions related to isolated chromatomes and methods of using them. Proteins and other factors that do not associate with chromatin in a cell but are present in a purified chromatome, e.g., due to limitations of purification methods, may be termed "non-chromatomal proteins" and "non-chromatomal factors", respectively.

The present application also provides an isolated chromatome comprising chromatomal proteins and chromatomal factors. By "isolated" is meant that the chromatome is separated from its natural environment, e.g., in the nucleus of a cell. In certain embodiments, the isolated chromatome comprises less than about 10%, based on molecular weight, for example, less than about 5%, based on molecular weight, non-chromatomal proteins and non-chromatomal factors.

The present application further provides a method for preparing a cross-linked nucleic acid-protein complex. The method can be employed to isolate a chromatome. In certain embodiments, the isolated chromatome comprises less than about 10%, for example, less than about 5%, non-chromatomal proteins and non-chromatomal factors. The method can comprise contacting a cell with a stabilizer at a concentration (which is the final concentration of the stabilizer in the stabilizing reaction mixture comprising the stabilizer and the molecules and/or compositions to be stabilized) and for a period of time effective for stabilizing protein-chromatin and/or protein-DNA complexes while mitigating the formation non-specific protein-protein complexes that occur in a typical ChIP assay. The concentration and the period of time are selected for specific stabilization of the interaction between chromatin and proteins and/or chromatin and DNA as well as for isolation protein-chromatin and/or protein-DNA complexes from the cell. The isolated protein-chromatin and/or protein-DNA complexes are formed by chromatomal proteins and chromatin as components of the isolated chromatome. The chromatome may further comprise other chromatomal factors, such as DNAs, RNAs, small molecules, and/or metabolites.

"Small molecule" as used herein, is meant to refer to a molecule or composition, which has a molecular weight of less that about 6 kD (e.g., less than about 2.5 kD).

A "metabolite" generally refers to a substance that takes part in the process of metabolism, which may involve the breakdown of complex organic constituents of the body with the liberation of energy for use in bodily functioning or the breakdown of exogenous substances (e.g., a drug administered to a patient). The various substances or compounds that take part in or are formed by these reactions are generally called "metabolites."

In certain embodiments, a chromatome is prepared or isolated from a eukaryotic cell.

In certain embodiments, the stabilizer employed for preparing the chromatome comprises a cross-linking agent. In certain embodiments, the cross-linking agent is less than, for example, about 1%, about 0.5%, about 0.2%, or about 0.1%, by volume formaldehyde. In a method, where formaldehyde is used as the stabilizer, the period of time for stabilizing protein-chromatin and/or protein-DNA complexes can be, for example, less than about 2 hours, about 1.5 hours, about 1 hour, about 30 minutes, about 20 minutes, about 15 minutes, about 10 minutes, about 5 minutes, about 3 minutes, or about 1 minute. The cross-linking for stabilizing protein-chromatin complexes may be carried out at different temperatures, e.g., ambient temperature, about 4° C., or on ice.

By way of example, cells can be placed in 0.1% by volume solution of formaldehyde and cross-linked for about 3 minutes. Cross-linking at this concentration of formaldehyde and for this period of time allows protein-chromatin and/or protein-DNA complexes in the cell to stabilize while mitigating while mitigating the formation non-specific protein-protein complexes.

In certain embodiments, cross-linking for stabilizing protein-chromatin and/or protein-DNA complexes can be achieved by UV radiation.

Other cross-linking agents may be employed to stabilize protein-chromatin and/or protein-DNA complexes. Cross-linking agents, sometimes also referred to as cross-linkers, may be homobifunctional (e.g., homobifunctional amine cross-linkers including, but not limited to, glutaraldehyde, bis(imido esters), bis(succinimidyl esters), diisocyanates and diacid chlorides), heterobifunctional, cleavable, non cleavable, amine reactive, sulfhydryl reactive, and photoreactive. For example, 1-Ethyl-3-(3-dimethylaminopropyl) carbodiimide (EDAC, E2247) can react with biomolecules to form "zero-length" cross-links, usually within a molecule or between subunits of a protein complex or components or a protein-DNA complex (Thomas J O, Sternberg N, Weisberg R. J Mol Biol 123, 149-161 (1978) PN19955).

In certain embodiments, the protein-chromatin complexes in a chromatome are isolated by cesium chloride (CsC1) gradient. Alternatively, the protein-chromatin complexes can be isolated by sucrose gradient. Other suitable separation/purification/isolation methods may also be employed to isolate and/or fractionate the protein-chromatin complexes, e.g., column chromatography, gel electrophoresis, etc.

The present application further provides a method for identifying chromatomal proteins in a biological sample, e.g., a cell. In certain embodiments, the method comprises isolating a chromatome from the biological sample. The isolated chromatome comprises chromatomal proteins and chromatomal factors, and less than about 10%, for example, less than about 5%, non-chromatomal proteins and non-chromatomal factors. The isolated chromatome can comprise protein-chromatin complexes formed by chromatomal proteins and chromatin. The method further comprises isolating one or more proteins from the protein-chromatin complexes in the isolated chromatome; and identifying the isolated proteins.

The present application also provides a method for identifying chromatomal factors in a cell. In certain embodiments, the method comprises isolating a chromatome from the biological sample. The isolated chromatome can comprise chromatomal proteins and chromatomal factors, and less than about 10%, for example, less than about 5%, non-chromatomal proteins and non-chromatomal factors.

The method further comprises isolating one or more chromatomal proteins and non-chromatomal factors. The method further comprises isolating one or more chromatomal factors from the isolated chromatome. The isolated factors are then identified. The isolated factors may be DNAs, RNAs, small molecules, or metabolites.

The present application also provides a method for identifying chromatomal proteins associated with a phenotype of a subject, e.g., a cell. In certain embodiments, the method comprises isolating a chromatome from a subject exhibiting the phenotype. The isolated chromatome can comprise chromatomal proteins and chromatomal factors, and less than about 10%, for example, less than about 5%, non-chromatomal proteins and non-chromatomal factors. The isolated chromatome can comprise protein-chromatin complexes formed by chromatomal proteins and chromatin. The method further comprises isolating one or more proteins from protein-chromatin complexes in the isolated chromatome. The isolated proteins are then identified and the identity of the isolated proteins is compared with the identity of chromatomal proteins from a subject that does not exhibit the phenotype (e.g., a control subject). The chromatomal proteins identified from the sample subject that are different from the chromatomal proteins from the control subject are associated with the phenotype.

The present application also contemplates a method for identifying chromatomal factors (e.g., DNAs, RNAs, metabolites) associated with a phenotype of a subject, e.g., a cell. Similar to the method above, the method can comprise isolating and identifying one or more chromatomal factors from a subject exhibiting a particular phenotype, and comparing with one or more chromatomal factors from a control subject.

The phenotype of a subject, e.g., a cell, may be associated with the cell type or tissue specificity (e.g., a B lymphocyte versus a T lymphocyte versus a smooth muscle cell), organism or species specificity (e.g., a human B lymphocyte versus a murine, canine, or porcine lymphocyte), cell growth or cell cycle stage (a cell at G0, G1, or cell cycle arrest), proliferative potential of the cell, or other physiological or non-physiological condition of the cell. Non-physiological condition may be a disease condition, e.g., a cell with or without metastatic potential (e.g., a malignant or benign tumor cell) or apoptotic potential (certain neural cells from a patient having a neurodegenerative condition or disease).

The present application further provides a method for determining the likelihood for a sample subject to develop a particular phenotype, which is useful in various diagnostic or screening applications. In certain embodiments, the method comprises profiling chromatomal proteins and/or chromatomal factors from the sample subject (to obtain a sample profile). The method further comprises comparing the sample profile with the profile of chromatomal proteins and/or chromatomal factors from a subject that exhibits the particular phenotype (or phenotypic profile). The higher level of identity between the sample profile and the phenotypic profile, the more likely that the sample subject will develop or exhibit the phenotype.

In certain embodiments, profiling the chromatomal proteins and/or chromatomal factors comprises identifying one or more chromatomal proteins or chromatomal factors.

In certain embodiments, profiling the chromatomal proteins and/or chromatomal factors comprises separation of the proteins and/or factors by gel-electrophoresis, and further analysis of gel-electrophoresis profiles or the separated proteins and/or factors.

In certain embodiments, profiling the chromatomal proteins and/or chromatomal factors comprises profiling the proteins and/or factors by chromatography. Chromatography generally refers to the separation of a mixture of substances by charge, size, or other property by allowing the mixture to partition between a moving phase and a stationary phase.

In certain embodiments, profiling the chromatomal proteins and/or chromatomal factors comprises profiling the proteins and/or factors by spectrometry.

In certain embodiments, profiling the chromatomal proteins and/or comprises assaying for biological activities of one or more proteins and/or factors.

The methods and compositions provided herein are thus useful in many applications, for example:

Identifying Novel Chromatomal Proteins and Factors.

Analysis of isolated or purified chromatomes and their components is likely to identify previously uncharacterized proteins and/or factors as binding to (or associated with) chromatin.

Organism-Specificity of Chromatomes.

Figure 5:
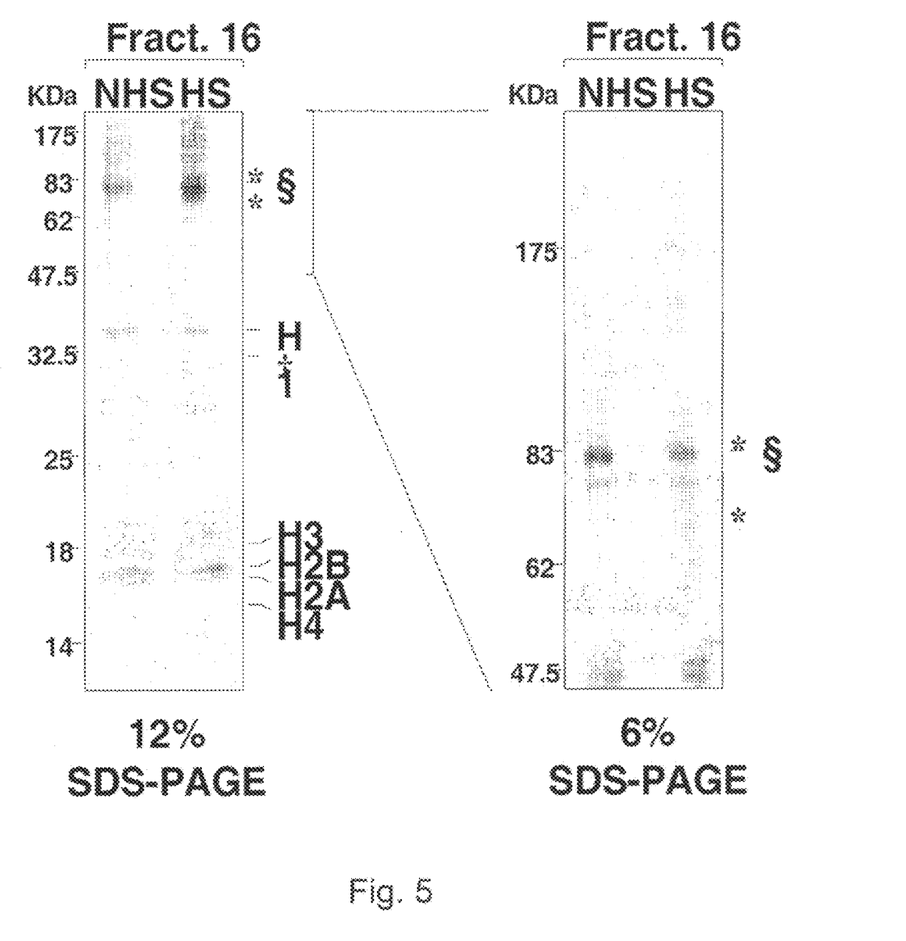
FIG. 5 illustrates the analysis by Coomassie blue staining of proteins present in Fraction 16 of the CsCl fractions of each *Drosophila* chromatome (NHS vs. HS).
Figure 6:
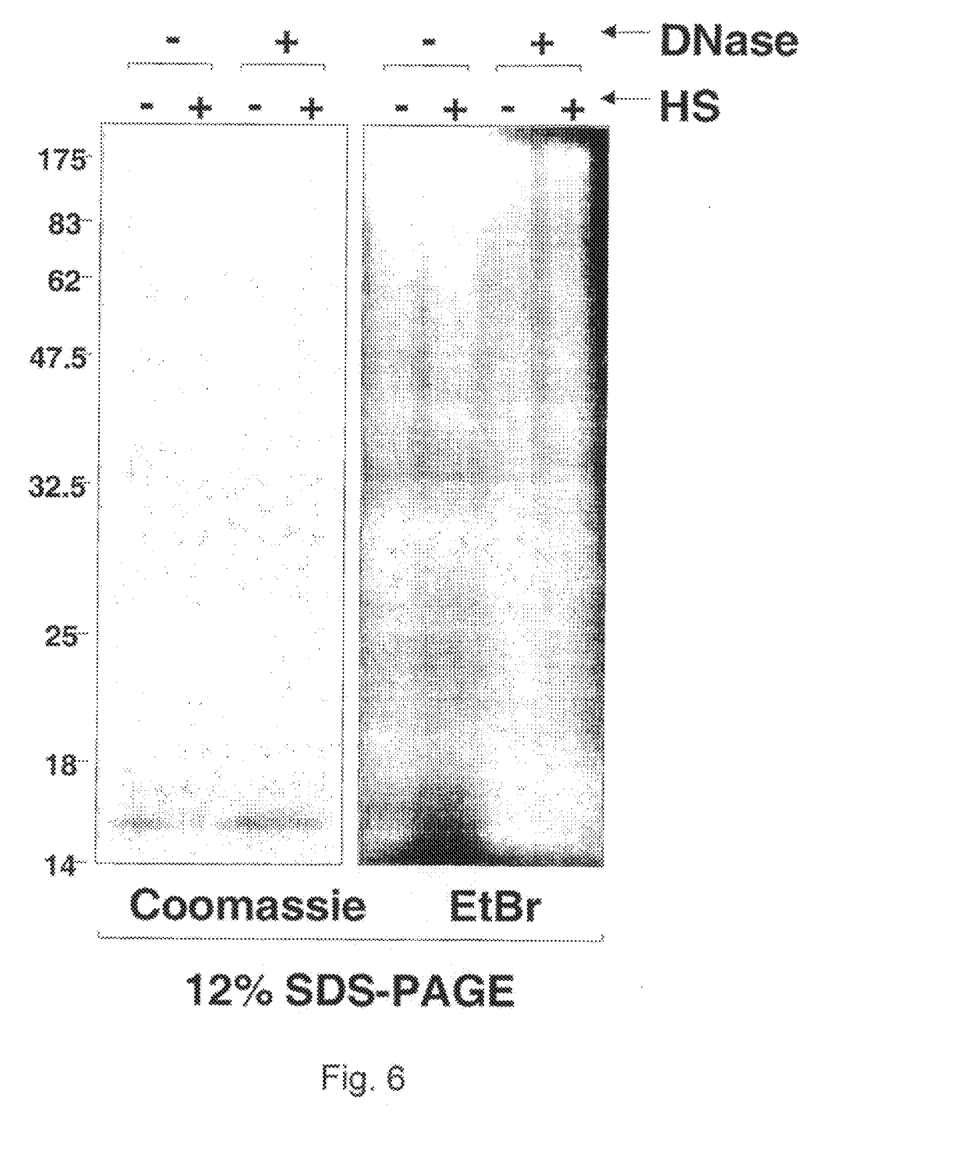
FIG. 6 illustrates the analysis of RNA associated with chromatin as present in Fraction 16 of the CsCl fractions.

As described in the Examples and FIG. 5, the *Drosophila* chromatome can be effectively purified from tissue culture cells. Similarly, chromatomes can be purified from other model eukaryotic systems such as plant, yeast, nematode, mouse, and mammalian cells. Although the core histones and H1 are predicted to omnipresent in all eukaryotes, other chromatome proteins and/or factors can be species-specific, which can be determined by the methods and compositions described herein.

Stress-Induced Chromatomes.

Figure 4:
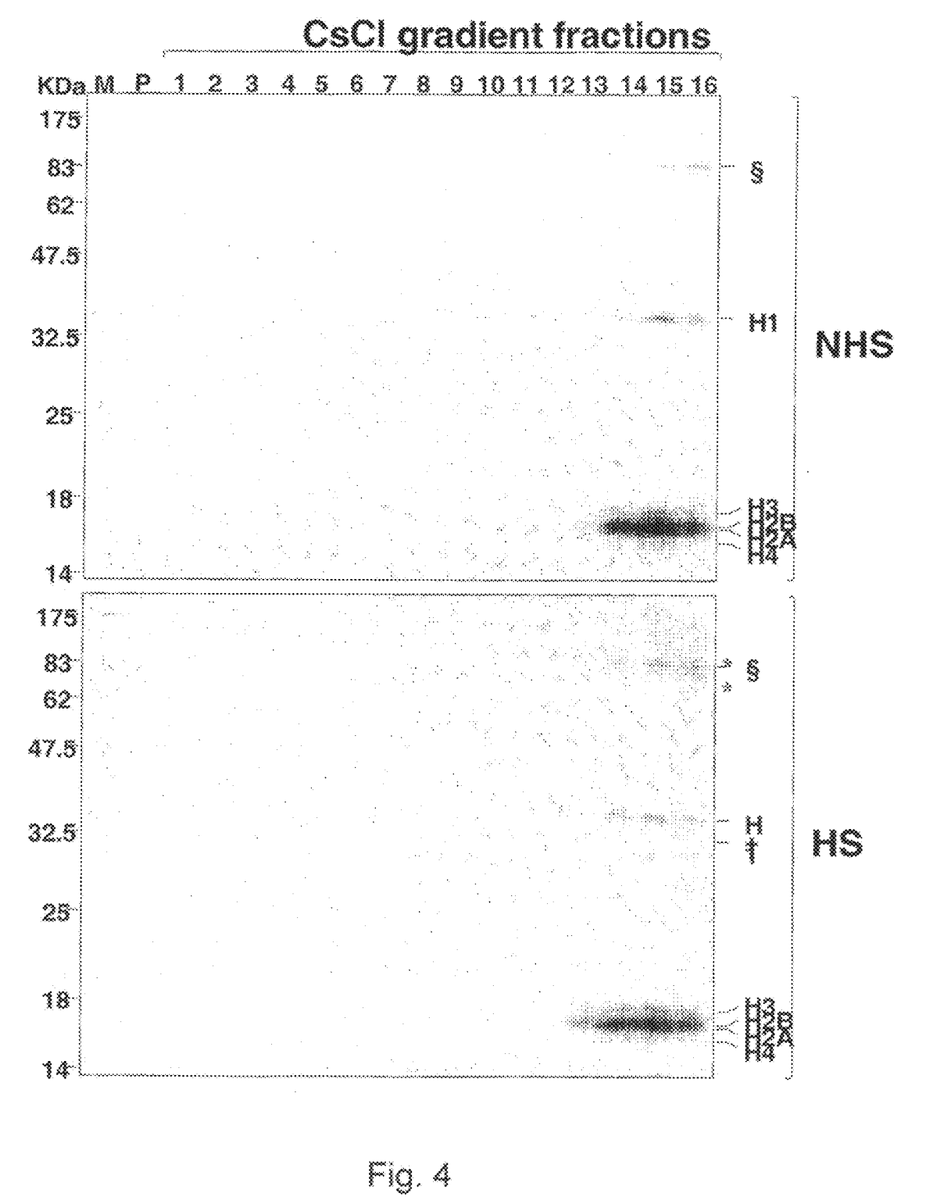
FIG. 4 illustrates the Coomassie blue staining of proteins present in the CsCl fractions.

As described in the Example and FIGS. 4 and 5, specific polypeptides associate or interact with the *Drosophila* chromatome in response to one particular stress, heat shock. Recruitment or eviction of chromatomal proteins and/or factors from the chromatome can also be detected in response to environmental cues or drugs that damage nucleic acids, modulate gene expression, or influence signal transduction cascades.

Effects of Apoptosis on Chromatomal Content.

Chromatin modification and DNA degradation are critical steps during programmed cell death. Analysis of chromatomes from apoptotic cells will help elucidate mechanisms and factors regulating cell death.

Chromatomes from Differentiated and Transformed Cells.

During stem cell maturation and in some transformed cells, changes in chromatin architecture occur concomitant with the change in the cell state. Comprehensive chromatome analysis of these cell types is made feasible by the methods and compositions described herein.

Development-, Organ-, and Tissue-specific Chromatomes.

Metazoans go through different defined developmental stages and form specialized organs and tissues, during which important chromatin reprogramming occurs. Defining the chromatome as a consequence of growth and tissue type is also made feasible by the methods and compositions described herein that allow comprehensive chromatome analysis.

Disease-Specific Chromatomes.

Several human diseases (e.g., cancer) result from defective chromatin structure and function. Chromatomes purified from disease tissues based on the methods described herein will allow comprehensive chromatome analysis to further elucidate and target the defects in chromatin structure and function.

Cell Cycle and the Chromatome.

Gene expression patterns oscillate in response to changes in chromatin remodeling during the cell cycle. Comprehensive analysis of chromatomes from cells at different stages of the cell cycle will allow further analysis and/or identification of the factors regulating gene expression and cell cycle progression.

Aging and the Chromatome.

It is well established that longevity regulation in yeast and other eukaryotes is in part modulated at the level of chromatin structure. Factors that regulate or modulate chromatin structure in an age-specific manner can also be detected in chromatomal preparations made feasible by the methods and compositions described herein.

Chromatomes from Infected Cells.

RNA viruses that integrate into host DNA cause changes in local and global chromatin structure. Chromatomes isolated or purified from infected cells may help identify chromatin targets impacted by viral genetic material.

Chromatomal Factor Post-translational Modifications.

The core histones are known to be phosphorylated, acetylated, methylated, and ubiquitylated on chromatin in response to environmental and developmental signals (He and Lehming, 2003). Thus, a chromatomal protein of interest can be specifically examined for its specific set of post-translational modifications under varying conditions.

Effects of Gene Mutants, Factor Depletion, or Factor Overexpression on Chromatomes.

Defects in basic biological processes can result from specific and direct perturbation of the organization and regulation of chromatin. Thus, chromatomes isolated from cells lacking, diminished for, or overexpressing a factor will provide invaluable information about the etiology of defective cellular control at the level of chromatin.

Comparative and Evolutionary Chromatomics.

DNA sequences from different organisms have created the field of comparative genomics. Similarly, comparative and evolutionary chromatomics studies can be carried by comparing a chromatome from one organism to that from a closely or distantly related organism.

System Chromatomics.

The comprehensive analysis and/or identification of chromatomal proteins and other factors in purified or isolated chromatomes makes it feasible to rebuild the chromatome from the ground up, or to deconstruct it from the top down, one protein and/or one factor at a time.

Further applications include the combination of the methods and compositions described herein with other technologies in the art. For example, chromatomography as described herein (e.g., a method for purifying or isolating a chromatome) can be coupled with immunoprecipitation (Chrip™) of a tagged or endogenous protein or of a protein modification (that is found on chromatin) to purify the unique protein complexes from the chromatome. Thus, Chrimp can be a powerful tool to define the composition, of, for example, transcription elongation, DNA repair, centromere-binding complexes.

Another application is to identify particular RNAs that associate with chromatin. In addition to characterizing the nascent transcripts present along active genes, small RNAs and regulatory RNAs are know to play roles in chromatin structure and gene expression. Thus, chromatin purification can be modified to uncover chromatin-associated RNAs, and the nascent transcripts can be analyzed by hybridization to microarrays.

Further applications may also include:

Analysis of Nuclear Factors not Associated with Chromatin.

Since CsC1 efficiently separates chromatin from RNA fractions, DNA fractions that are sub-stoichiometric or lacking for histones, and soluble nuclear material, one may discriminate protein complexes associating with RNA, naked DNA, and found in the soluble nucleoplasm.

Chromatomography and Drug Screening.

This approach can be used as a tool to screen for drugs that modulate chromatin structure or the chromatome or drugs that target particular chromatomal proteins and/or factors that associated with a particular phenotype of a cell.

Structural Analysis of Purified Chromatomes of Purified Chromatomal Complexes.

Electron microscopy studies and/or other structural biology approaches (e.g., scanning or atomic force microscopy on these information-rich chromatomal materials may provide insight into higher-order chromatin structures and the structures of molecular machines on DNA.

Purification of Specific DNA Sequence and its Associated Proteins.

Additional affinity chromatographic tools may be utilized to selectively isolate DNA sequences of interest (e.g., a specific cancer gene, a telomere on one particular chromosome, etc.) to which a protein complex binds.

Accordingly, chromatomics may be applied to any biological process that impinges on, directly or indirectly, poorly or robustly, acutely or chronically, and globally or locally on chromatin structure and function. The chromatome of every organism and for every disease, mutation, insult, or process that globally affects chromatin structure should be pursued vigorously (and has been made feasible by the present application), because these avenues of research are bound to yield not only basic biology but also a plethora of targets for therapeutic intervention.

The invention now being generally described, it will be more readily understood by reference to the following examples, which are included merely for purposes of illustration of certain aspects and embodiments of the present invention, and are not intended to limit the invention.

EXAMPLE

Chromatin Purification

Figure 1:
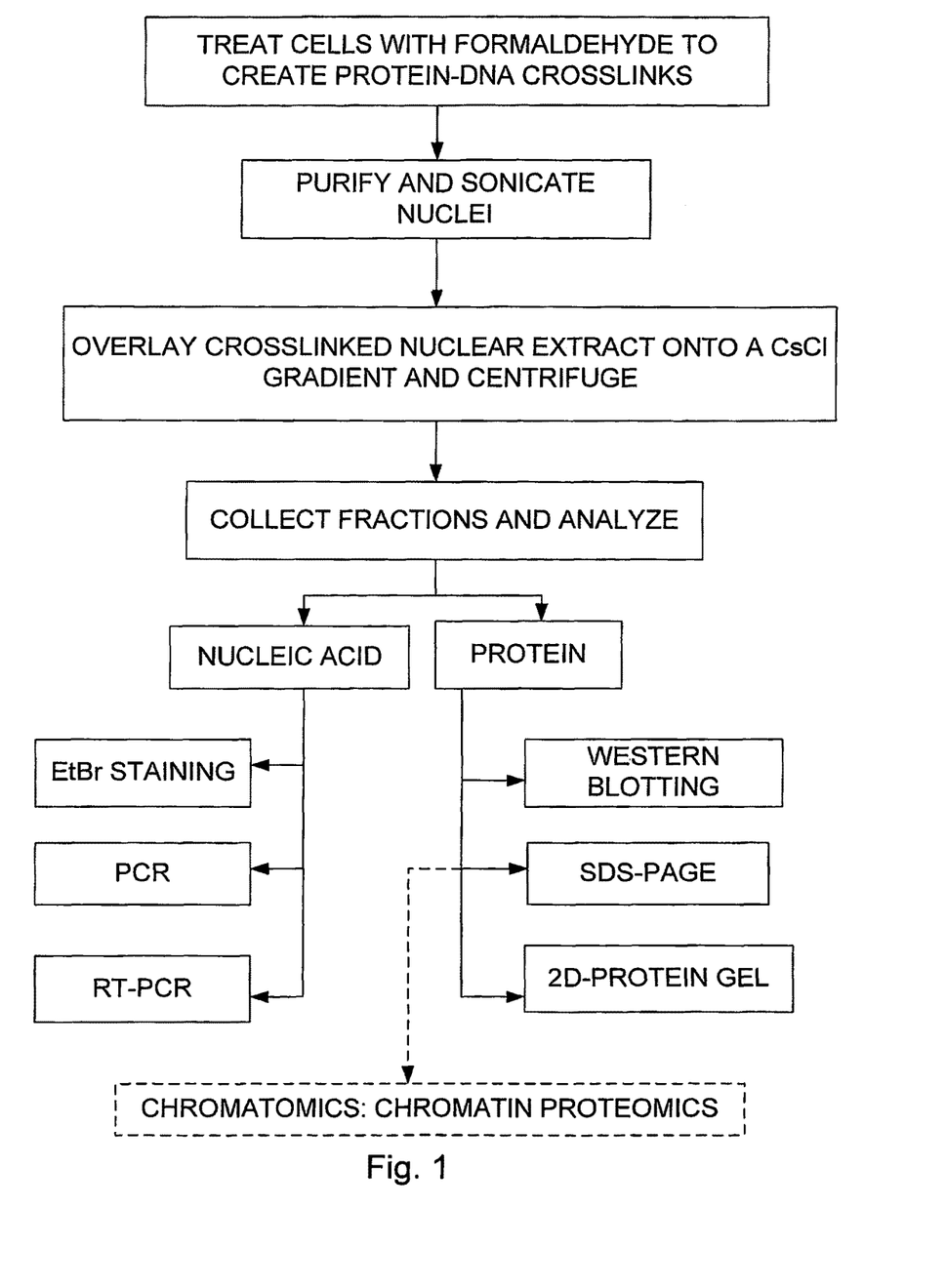
FIG. 1 illustrates a flow chart of a method of chromatome purification and characterization.

FIG. 1 is a schematic flow diagram illustrating a method of purification of *Drosophila* chromatome. *Drosophila melanogaster* S2 embryonic tissue culture cells were grown HyQ-CCM3 media (HyClone). Cells were grown in a spinner flask to a density of $1 \times 10^7$ cells/ml. (The solution volumes in this protocol will be varied dependent upon the size of culture to be processed. This has been optimized already for different amounts of *Drosophila* cells.) Cells were removed from the spinner flask and placed into an Erlenmeyer flask and formaldehyde was added to a final concentration of 0.1% by volume. Cells were cross-linked for 3 minutes on the bench top before the formaldehyde was quenched with the addition of glycine to a final concentration of 125 mM.

Formaldehyde is commonly used at a final concentration of 1% for 1 hour in other cell types. The low concentration and treatment time in this protocol can greatly reduce significant amounts of nonspecific protein-protein and protein-nucleic acid cross-links.

Cross-linked cells were centrifuged at 5000 rpm for 10 minutes at 4° C. and cell pellets were resuspended in lysis buffer A (100 mM KCl, 50 mM NaCl, 5 mM-$MgCl_2$, 10 mM Tris-HCl (pH 8.0)). Cells were lysed with the addition of the non-ionic detergent NP-40 to a final concentration of 1% and nuclear pellets were obtained following centrifugation at 5000 rpm for 10 minutes at 4° C. Then, nuclei were isolated, resuspended in lysis buffer B (100 mM NaCl, 10 mM Tris (ph 80.), 1 mM EDTA, 01.% NP-40), and lysed in 2% sarkosyl detergent. Lysed nuclei were then sonicated (Misonix 3000) with 10-20 15 second intermittent bursts with 15 seconds on ice in between bursts. Lysed cross-linked nuclear extract was then overlaid onto a cesium chloride step gradient (1.3 g/ml, 1.5 g/ml, 1.75 g/ml) and subjected to ultracentrifugation (rotor, speed, and time dependent upon cell number processed) at 25° C. Following this, an 18 gauge needle was used to poke a hole in the bottom of the ultracentrifugation tube and fractions are collected in eppendorf tubes.

The "top" fraction is the last fraction that can be collected before a viscous layer perturbs flow of material. This viscous material represents cross-linked protein complexes. Above this layer are several additions fractions, containing soluble non-chromatin-associated factors. These different fractions are not described here but will be discussed below. Fractions were then independently and exhaustively (3×2 L, 6 hours each) dialyzed in dialysis buffer (50 mM Tris (pH 8.0), 2 mM EDTA) at 4° C. Fractions were then aliquoted into independent eppendorf tubes and subjected to further analysis Chromatome Analysis:

Both the nucleic acid and protein content of chromatin was analyzed.

Figure 2:
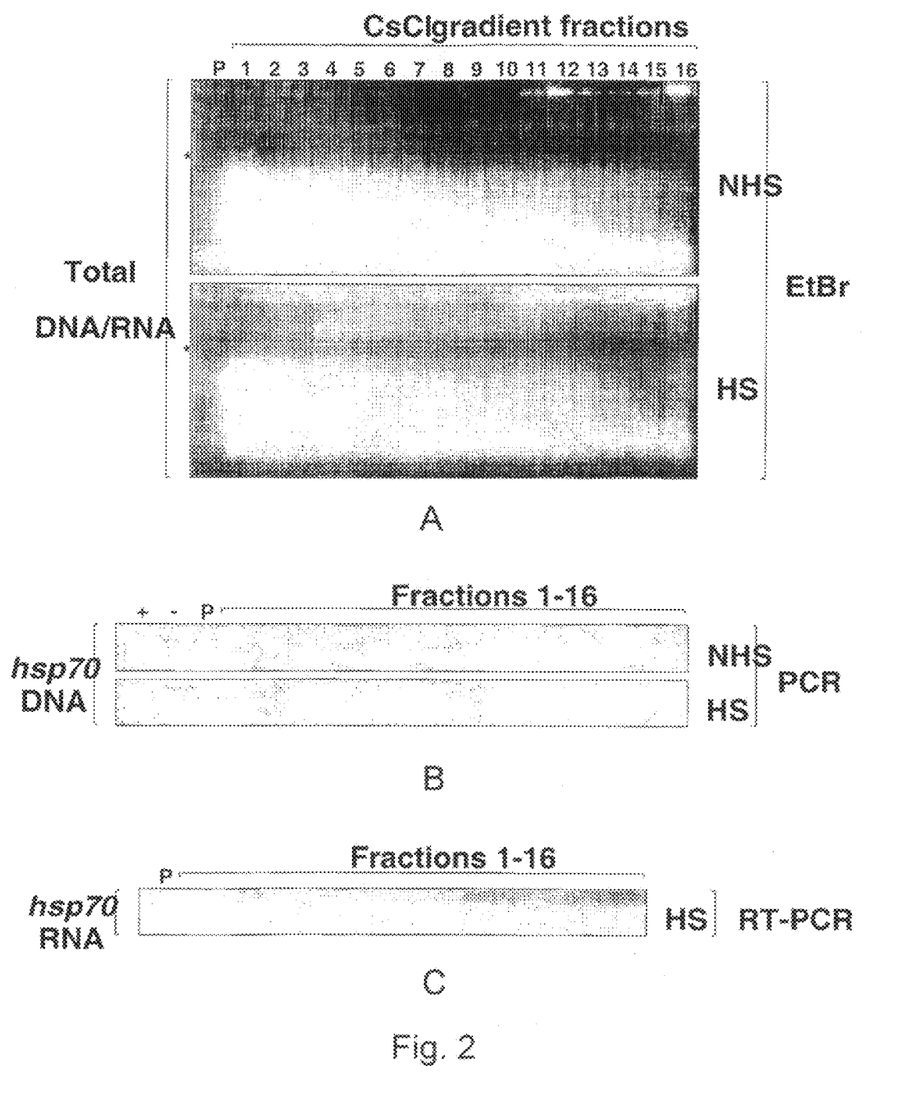
FIG. 2A illustrates the gel electrophoresis analysis of total nucleic acid content of chromatin purified from non-heat shocked (NHS) cells or cells subjected to a 30-minute heat shock (HS).
FIG. 2B illustrates the detection of DNA in the CsCl fractions.
FIG. 2C illustrates reverse transcriptase-PCR (RT-PCR) amplification of hsp70 mRNA in the CsCl fractions.

Nucleic Acid Analyses:

Ethidium bromide (EtBr) was used to detect total nucleic acids purified from cells that have or have not been heat shocked (FIG. 2A). Since EtBr staining detects both DNA and RNA, I wanted to determine where a transcriptionally inducible gene resided in the gradient fractions. To this end, I performed polymerase chain reaction (PCR) using primers to amplify the DNA for heat shock gene hsp70 (FIG. 2B). The majority of this gene, which is activated in response to heat shock, localizes towards to top of the gradient, irrespective of whether or not the cells are heat shocked. In contrast, hsp70 RNA is found near the bottom of the gradient, as detected by reverse transcriptase PCR (RT-PCR) (FIG. 2C). The small amount of hsp70 RNA found near the top of the gradient in fractions that co-fractionates with the hsp70 DNA most likely represents nascent transcripts.

Figure 3:
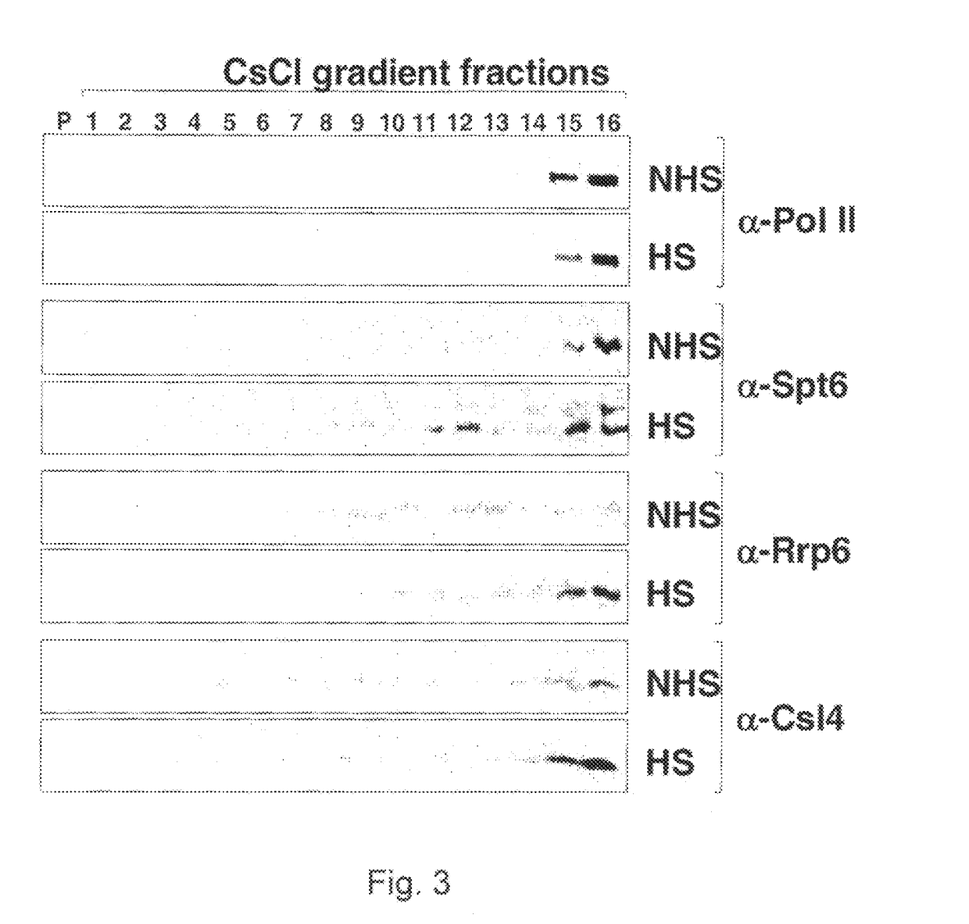
FIG. 3 illustrates the western-blotting detection of certain known chromatin-associated factors in the CsCl fractions. NHS: non-heat shocked sample; HS: heat shocked sample.

Protein Analysis:

To determine to what extent protein was associated with the purified chromatin, I tested for the presence of known chromatin-associated factors using western blotting (FIG. 3). RNA polymerase II (Pol II), the engine that drives mRNA production, Spt6, a factor involved in transcription elongation and chromatin structure, Rrp6, an exoribonuclease involved in co-transcriptional mRNA surveillance, and Cs14, a factor with roles in mRNA surveillance and centromere biology, all cross-link to chromatin, with the majority of these factors in fractions coincident with the DNA corresponding to the gene unit of hsp70 (FIGS. 3 and 2B). (All of these factors associate with chromosomes and are present at hsp70 as demonstrated by the ChIP assay. Although Pol II is most enriched at the top of the gradient (where presumptive nascent hsp70 transcripts are, see FIG. 2B), Cs14 is found throughout the gradient. This latter point indicates that different protein DNA complexes may be found in distinct fractions.

To examine global protein occupancy on purified chromatin, fractions were analyzed by Coomassie staining (FIG. 4). Proteins were found throughout the gradient, with most of the factors at the top of the gradient. A striking similarity, and consistency of banding patterns was observed in non-heat shock and heat shock chromatin. However, 2 bands representing unidentified factors of approximately 70 and 83 kDa are enriched on chromatin in response to heat shock; in addition, at least one band is diminished in the chromatome following heat shock. The diagnostic Coomassie staining pattern of the core histones H2A, H2B, H3, and H4 is also present in these preparations, with the stoichiometric factor at 34 kDa predicted to be H1. A close inspection of the protein content of the chromatin of fraction 16 from non-heat and heat shock samples shows that an additional set of factors that are substoichiometric to the histones are apparently stoichiometric with one another (FIG. 5). The identity of these factors can be ascertained by further analysis.

Figure 7:
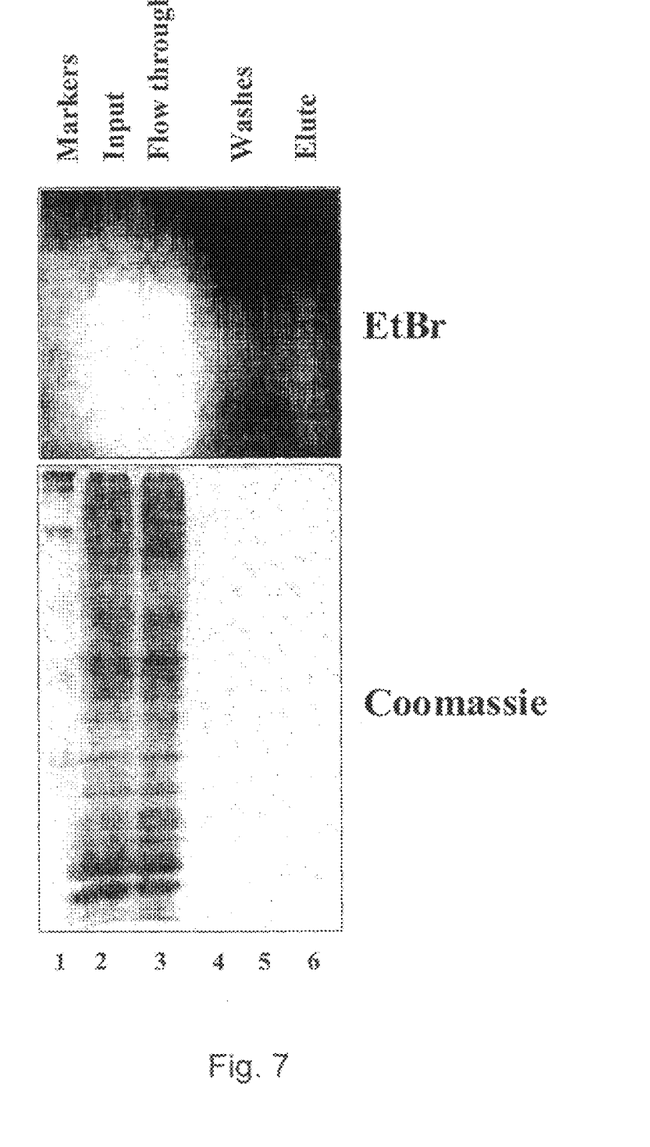
FIG. 7 illustrates the analysis of chromatome fraction that was loaded in Qiagen miniprep column.

FIG. 7 illustrates that enriched and concentrated chromatome fraction in 1×TE that was loaded onto a Qiagen miniprep column. The chromatome is not retained by the Qiagen miniprep column. Note that the majority of DNA and protein are recovered in the flow-through of the column (lane 3) rather than the eluate (lane 6).

Further Analysis:

Although CsC1 is efficient at separating protein-DNA complexes based upon their buoyant density, it does not separate them based upon size or shape. In order to accomplish this, chromatome fractions can be pooled and subjected to either glycerol or sucrose gradient sedimentation. Further examination of these protein bands by two-dimensional protein gels can provide a more accurate accounting of the number of chromatomal factors those factors that change in response to heat shock. Lastly, mass spectrometry can be employed to learn the identity of the *Drosophila* chromatome. Once proteins have been identified, roles in chromatin structure and function will be verified by immunofluorescence, chromatin and protein complex immunoprecipitation, and depletion studies.

Having described the invention, the following is claimed:
1. A method for identifying chromatomal proteins associated with a phenotype of a cell comprising:
   isolating a chromatome from a eukaryotic cell exhibiting the phenotype, and including at least one of H1, H2A, H2B, H3, and H4, wherein the isolated chromatome comprises chromatomal proteins and chromatomal factors, and less than 10% non-chromatomal proteins and non-chromatomal factors, and wherein the isolated chromatome comprises protein-chromatin complexes;
   isolating proteins from protein-chromatin complexes in the isolated chromatome;
   identifying the isolated proteins; and
   comparing the identity of the isolated proteins with the identity of chromatomal proteins from a cell that does not exhibit the phenotype; wherein the isolated chromatomal proteins associated with the phenotype are different from the chromatomal proteins from the cell that does not exhibit the phenotype, wherein the chromatome is isolated by contacting a cell with a stabilizer at a concentration and for a period of time effective for stabilizing protein-chromatin complexes, the concentration and the period of time being selected for specific stabilization of the interactions between chromatiome proteins and chromatin while mitigating formation of non-specific protein-protein and protein-nucleic acid complexes; the stabilizer being a cross-linking agent comprising formaldehyde at a concentration of about 0.1% by volume, and the period of time being less than 5 minutes.

2. The method of claim 1, the isolated proteins being identified by gel-electrophoresis.

3. The method of claim 1, the isolated proteins being identified by chromatography.

4. The method of claim 1, the isolated proteins being identified by spectrometry.

5. The method of claim 1, the isolated proteins being identified by assays for biological activities of one or more proteins.

6. The method of claim 1, the protein-chromation complexes being isolated by CsCI gradient.

7. The method of claim 1, the protein-chromatin complexes being isolated by sucrose gradient.

8. The method of claim 1, the protein-chromatin complexes being isolated by chromatography.

\* \* \* \* \*

UNITED STATES PATENT AND TRADEMARK OFFICE
CERTIFICATE OF CORRECTION

PATENT NO.        : 9,522,941 B2
APPLICATION NO.   : 11/909677
DATED             : December 20, 2016
INVENTOR(S)       : Andrulis Page 1 of 1

It is certified that error appears in the above-identified patent and that said Letters Patent is hereby corrected as shown below:

In the Claims

Column 10, Line 40 Claim 1 delete "phenotype of a cell" and insert --phenotype of a eukaryotic cell--

Column 10, Line 48 Claim 1 delete "isolating proteins" and insert --isolating chromatomal proteins--

Column 10, Line 50 Claim 1 delete "isolated proteins" and insert --isolated chromatomal proteins--

Column 10, Line 51 Claim 1 delete "isolated proteins" and insert --isolated chromatomal proteins--

Column 10, Line 61 Claim 1 delete "between chromatiome" and insert --between chromatome--

Signed and Sealed this
Fourth Day of April, 2017

Michelle K. Lee
*Director of the United States Patent and Trademark Office*